United States Patent [19]

Kaplan et al.

[11] 4,360,523

[45] Nov. 23, 1982

[54] PHARMACEUTICAL FORMULATIONS OF 4'-(9-ACRIDINYLAMINO)-METHANESULFON-M-ANISIDIDE

[75] Inventors: Murray A. Kaplan, Syracuse, N.Y.; Daniel Bouzard, Franconville, France; Claude Perol, Paris, France; Jacques Stemer, Paris, France; Abraham Weber, Paris, France

[73] Assignee: Bristol-Myers Company, New York, N.Y.

[21] Appl. No.: 147,056

[22] Filed: May 16, 1980

[51] Int. Cl.³ .......................................... H61K 31/435
[52] U.S. Cl. ..................................................... 424/257
[58] Field of Search ......................................... 424/257

[56] References Cited
PUBLICATIONS

Cain et al., Europ. J. Cancer, 10:539–540, (1974).
Chemical Abstracts 67:14819u, (1967).
Weiss et al., Cancer Clin. Trials 3:203–209, 1980.
FDC Reports, Nov. 3, 1980, pp. 6–7.
Issell, Cancer Treatment Reviews (198) 7, 73–83.
Von Hoff et al., Cancer Treatment Reports 62(10), 1421–1426, (Oct. 1978).

*Primary Examiner*—Jerome D. Goldberg
*Attorney, Agent, or Firm*—David M. Morse

[57] ABSTRACT

This invention concerns novel water-soluble compositions of 4'-(9-acridinylamino)-methanesulfon-m-anisidide (m-AMSA). More particularly, water-soluble compositions are provided which comprise a mixture of m-AMSA with lactic acid. The compositions enable m-AMSA to be administered as an aqueous solution without the necessity of using dimethylacetamide as a pharmaceutical vehicle.

9 Claims, No Drawings

PHARMACEUTICAL FORMULATIONS OF 4'-(9-ACRIDINYLAMINO)-METHANESULFON-M-ANISIDIDE

BACKGROUND OF THE INVENTION

1. Field of the Invention

The novel compositions of the present invention possess the advantageous pharmacological properties of the known free base compound and in addition have unexpectedly high water-solubility, thus allowing preparation of useful dosage forms for intravenous administration.

2. Description of the Prior Art

The acridine derivative m-AMSA [4'-9-acridinylamino)methanesulfon-m-anisidide] has been reported by Cain, et al. in *Europ. J. Cancer* 10:539–549 (1974) to possess significant antitumor activity in animal tumor systems.

When an antitumor agent such as m-AMSA is employed for pharmaceutical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water solubility also facilitates preparation of oral and non-intravenous parenteral dosage forms. Thus, it is decidedly advantageous if a therapeutic agent is water-soluble, particularly when one considers that the most direct route for achieving therapeutic blood levels of a drug is by intravenous administration.

The free base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble. The formulation presently consists of two sterile liquids combined just prior to use. A solution of m-AMSA in anhydrous N,N-dimethylacetamide is contained in an ampule. A separative vial contains an aqueous L(+)-lactic acid solution for use as a diluent. When mixed the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide water-soluble, stable, therapeutically acceptable forms of m-AMSA which can be administered intravenously (as well as by other routes) and which do not contain or require dimethylacetamide as a pharmaceutical vehicle. This object as well as other features and advantages of the invention will be readily apparent to those skilled in the art from the disclosure set out below.

SUMMARY OF THE INVENTION

The present invention provides stable, solid, water-soluble compositions for reconstitution with water or an aqueous vehicle as stable solutions of m-AMSA, said compositions comprising a mixture of m-AMSA and lactic acid, the molar ratio of the lactic acid to m-AMSA being from about 1.5:1 to about 4:1.

Also provided are processes for preparing the above-described compositions.

DETAILED DESCRIPTION

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts as well as from solubility tests carried out by the present inventors on salts such as the levulinate, citrate and lactobionate (all such salts being soluble at <5 mg/ml).

In investigating solubility properties of m-AMSA acid addition salts, we have prepared the crystalline L(+)-monolactate salt of m-AMSA (crystallized out of ethanol) and have found that it too is insufficiently water-soluble at room temperature to provide an acceptable aqueous solution for intravenous administration. Surprisingly and unexpectedly, however, we have found that a solid dosage form comprising a mixture of about one mole of m-AMSA base per 1.5 to 4 moles of lactic acid possesses the highly desirable solubility, reconstitution and stability problems necessary for use as an intravenous drug.

The above-described solid compositions may be employed in the form of either a dry-fill (mixture of dry components) or lyophilized product. The solid dosage form may be conveniently and rapidly reconstituted with water or a sterile aqueous vehicle to provide at least a 5 mg/ml true solution of m-AMSA having excellent stability characteristics.

Preparation of the water-soluble compositions of the present invention as a dry-fill mixture may be accomplished by simply mixing the appropriate starting materials in the proper proportions. Thus, the m-AMSA/lactic acid composition is prepared by mixing m-AMSA base and D(−)- or L(+)-lactic acid in a ratio of about 1.5 to 4 moles of lactic acid per mole of m-AMSA. A preferred embodiment comprises a mixture of about 1.5 to 2.5 moles of lactic acid per mole of m-AMSA.

Preparation of the water-soluble compositions as a lyophilized mixture may be accomplished by subjecting an aqueous solution of the appropriate starting materials in the proper proportions to a standard lyophilization process. Thus, the lyophilized m-AMSA/lactic acid product is prepared by forming an aqueous solution of m-AMSA and lactic acid (D(−)-, L(+)- or DL-lactic acid) in a ratio of from about 1.5 to 4 (preferably 1.5 to 2.5) moles of lactic acid per mole of m-AMSA base and then lyophilizing said aqueous solution to obtain the desired solid composition. Before the lyophilization step, the aqueous solution is preferably filtered to remove any insoluble impurities. Also, conventional excipients such as mannitol may be added to facilitate dissolution of the lyophilized product. Lyophilization may be carried out in conventional laboratory or industrial lyophilizers according to methods well-known to those skilled in the art.

For preparation of unit dosage forms of the present compositions, the m-AMSA base may be used in any therapeutically effective dose. A suggested dosage range of m-AMSA base in a unit dosage form is from about 20–200 milligrams.

The dry-fill and lyophilized compositions provided by the present invention exhibit substantially the same pharmacological properties as the prior art m-AMSA forms. Because of their high water-solubility, however, they may be used to prepare dosage forms for intravenous administration which do not contain an undesirable pharmaceutical vehicle such as dimethylacetamide. The compositions may be used to prepare a single vial dry-fill or lyophilized product for reconstitution with sterile water or sterile aqueous vehicle as a parenteral dosage form.

The compositions of the present invention may be used to prepare oral or non-intravenous parenteral dosage forms as well as the preferred intravenous injectable product. The compositions have acceptable stability, both in solid form and in aqueous solution, to permit administration of an effective dose of m-AMSA in a relatively small volume of parenteral solution, thus allowing for bolus i.v. injections.

The compositions of the present invention may be administered either orally or parenterally, but preferably parenterally, in dosages (adjusted for amount of m-AMSA activity) and according to regimens previously disclosed in the literature. A particularly preferred dosage form is a reconstituted aqueous solution having 5 mg/ml of m-AMSA activity.

The following examples are given in illustration of, but not in limitation of, the present invention.

EXAMPLE 1

Lyophilization of m-AMSA and L(+)-Lactic Acid m-AMSA base (100 mg) and L(+)-lactic acid (50.33 mg) are dissolved in 10 ml of water. The resulting solution is filtered through a 0.22μ filter for clarification. The filtrate is then added to suitable flint glass vials (e.g. 5 ml solution per vial). The vials are partially stoppered and subjected to lyophilization at the following parameters:
  prefreezing at −55° C.;
  freezing at −50° C. for 2 hours;
  sublimation at −40° C. for about 68 hours at a pressure of about $4 \times 10^{-2}$ torr; and
  drying at +30° C. for about 48 hours.
The vials are then stoppered under vacuum or nitrogen atmosphere and sealed.

The lyophilized composition can be reconstituted with water to give (at room temperature) at least a 5 mg/ml solution of m-AMSA activity. Reconstitution time is about 3 minutes. Lyophilized vials were found to have acceptable stability after one month storage at 37° C. and 56° C.

EXAMPLE 2

Lyophilization of m-AMSA and L(+)-Lactic Acid m-AMSA base (150 mg) was slurried in 20 ml of sterile water. To the above two equivalents of L(+)-lactic acid (75 mg) were added and a complete solution was obtained. The solution was filtered through a 0.22 micron Millipore filter. Three 5 ml portions were lyophilized in 17.5 cc flint bottles for 24 hours on a laboratory lyophilizer to give a solid product. The product could be reconstituted with water to 7.5 and 5 mg/ml m-AMSA activity solutions which remained clear for at least 24 hours.

EXAMPLE 3

Dry-fill Mixture of m-AMSA and L(+)-Lactic Acid m-AMSA base (100 mg) and L(+)-lactic acid (47 mg; 2 equivalents) were mixed in a 50 cc flint vial.

To the above dry-fill product, 19 ml of sterile water was added and a 5 mg/ml solution of m-AMSA activity was obtained in 1–3 minutes of shaking at 16.5° C. The solution remained clear for at least 24 hours.

EXAMPLE 4

Lyophilization of m-AMSA and DL-Lactic Acid m-AMSA base (150 mg) was slurried in 16.5 ml of sterile water at 18° C. To the above 3.5 ml of a 20% DL-lactic acid solution (70 mg of DL-lactic acid; two equivalents) was added with stirring. The mixture was stirred for 10 minutes to give a pH 3.9 solution. The solution was passed through a 0.22 micron Millipore filter. One ml portions of the filtered solution were added to 8.5 ml flint vials and lyophilized on the laboratory lyophilizer for 24 hours.

The lyophilized product was reconstituted with sterile water to give a 7.5 mg/ml solution of m-AMSA activity which remained clear for at least 24 hours at room temperature.

Alternatively, a mixture of 35 mg L(+)-lactic acid and 35 mg D(−)-lactic acid can be used.

EXAMPLE 5

Dry-fill Mixture of m-AMSA and D(−)-Lactic Acid

A mixture was prepared of the following ingredients:

| | |
|---|---|
| m-AMSA base | 100 mg |
| D(−)-lactic acid (1.5 equivalents) | 35 mg. |

EXAMPLE 6

Lyophilization of m-AMSA and D(−)-Lactic Acid

A lyophilized product was prepared of the following composition using the general procedure of Example 2.

| | |
|---|---|
| m-AMSA base | 150 mg |
| D(−)-lactic acid (2 equivalents) | 75 mg. |

We claim:

1. A solid pharmaceutical composition for reconstitution with water to give a stable aqueous solution of m-AMSA, said composition consisting of m-AMSA having the formula

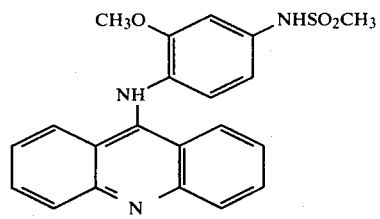

in admixture with lactic acid, the molar ratio of lactic acid to m-AMSA being from about 1.5:1 to 4:1.

2. A composition according to claim 1 wherein the molar ratio of lactic acid to m-AMSA is from about 1.5 to 2.5:1.

3. A composition according to claim 1 or claim 2 wherein the lactic acid is D(−)-lactic acid.

4. A composition according to claim 1 or claim 2 wherein the lactic acid is L(+)-lactic acid.

5. A composition according to claim 1 or claim 2 wherein the lactic acid is DL-lactic acid.

6. A solid pharmaceutical composition in unit dosage form for reconstitution with water to give a stable aqueous solution of m-AMSA, said composition consisting of a mixture of about 20 to 200 milligrams of m-AMSA having the formula

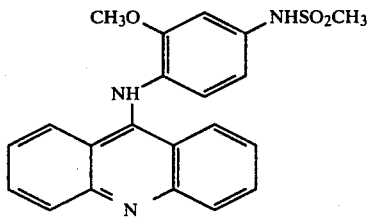

in admixture with about 1.5 to 4 molar equivalents of lactic acid.

7. A composition according to claim 6 wherein the lactic acid is L(+)-lactic acid.

8. A composition according to claim 6 wherein the lactic acid is D(−)-lactic acid.

9. A composition according to claim 6 wherein the lactic acid is DL-lactic acid.

* * * * *